(12) United States Patent
Flynn

(10) Patent No.: US 9,240,648 B2
(45) Date of Patent: Jan. 19, 2016

(54) HEADER CONTACT FOR AN IMPLANTABLE DEVICE

(71) Applicant: Cardiac Pacemakers, Inc., St. Paul, MN (US)

(72) Inventor: David M. Flynn, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 192 days.

(21) Appl. No.: 13/910,714

(22) Filed: Jun. 5, 2013

(65) Prior Publication Data
US 2013/0344751 A1 Dec. 26, 2013

Related U.S. Application Data

(60) Provisional application No. 61/664,468, filed on Jun. 26, 2012.

(51) Int. Cl.
| | |
|---|---|
| *H01R 13/33* | (2006.01) |
| *H01R 13/62* | (2006.01) |
| *H01R 43/00* | (2006.01) |
| *A61N 1/375* | (2006.01) |
| *H01R 13/187* | (2006.01) |
| *H01R 13/24* | (2006.01) |
| *H01R 24/58* | (2011.01) |

(52) U.S. Cl.
CPC ............. *H01R 13/62* (2013.01); *A61N 1/3752* (2013.01); *H01R 13/187* (2013.01); *H01R 13/2421* (2013.01); *H01R 24/58* (2013.01); *H01R 43/00* (2013.01); *Y10T 29/49208* (2015.01)

(58) Field of Classification Search
CPC .... H01R 13/62; H01R 24/58; H01R 13/2421; H01R 43/00; H01R 13/187; A61N 1/3752; Y10T 29/49208
USPC ............. 439/840, 843, 841, 842, 909; 29/876
See application file for complete search history.

(56) References Cited

U.S. PATENT DOCUMENTS

| | | | |
|---|---|---|---|
| 5,730,628 A | 3/1998 | Hawkins | |
| 6,241,759 B1 * | 6/2001 | Piplani et al. | ................ 623/1.11 |
| 8,032,221 B2 * | 10/2011 | Wengreen et al. | ............... 607/37 |
| 2002/0107555 A1 | 8/2002 | Rusin et al. | |

(Continued)

FOREIGN PATENT DOCUMENTS

| | | |
|---|---|---|
| CN | 104540545 A | 4/2015 |
| EP | 0723789 A1 | 7/1996 |

(Continued)

OTHER PUBLICATIONS

"International Application Serial No. PCT/US2013/044307, International Preliminary Report on Patentability mailed Jan. 8, 2015", 7 pgs.

(Continued)

*Primary Examiner* — Javaid Nasri
(74) *Attorney, Agent, or Firm* — Schwegman Lundberg & Woessner, P.A.

(57) ABSTRACT

An implantable medical device includes a housing and a header mounted to the housing, the header including a header body having a bore with an electrical contact located within the bore, wherein the electrical contact includes a helical coil spring having an axial bore, wherein the axial bore of the helical coil spring is aligned with a longitudinal axis of the bore.

16 Claims, 7 Drawing Sheets

(56) References Cited

U.S. PATENT DOCUMENTS

2011/0190719 A1* 8/2011 Kamen ............... A61F 5/44 604/335
2011/0281450 A1 11/2011 Loke et al.

FOREIGN PATENT DOCUMENTS

WO  WO-2011118656 A1  9/2011
WO  WO-2014004005 A1  1/2014

OTHER PUBLICATIONS

"International Application Serial No. PCT/US2013/044307, International Search Report mailed Aug. 28, 2013", 4 pgs.

"International Application Serial No. PCT/US2013/044307, Written Opinion mailed Aug. 28, 2013", 5 pgs.

"Japanese Application Serial No. [Pending], Amendment filed Feb. 19, 2015", With English Claims, 22 pgs.

* cited by examiner

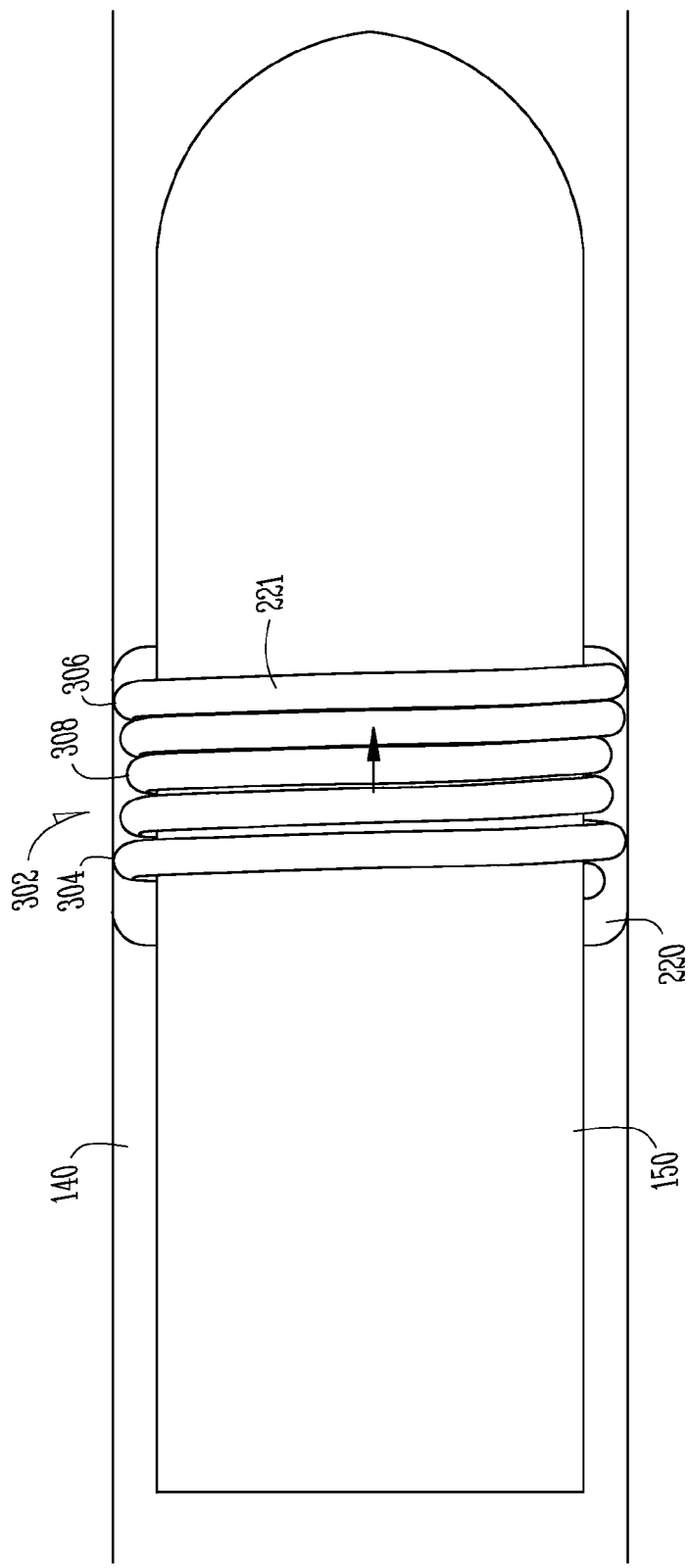

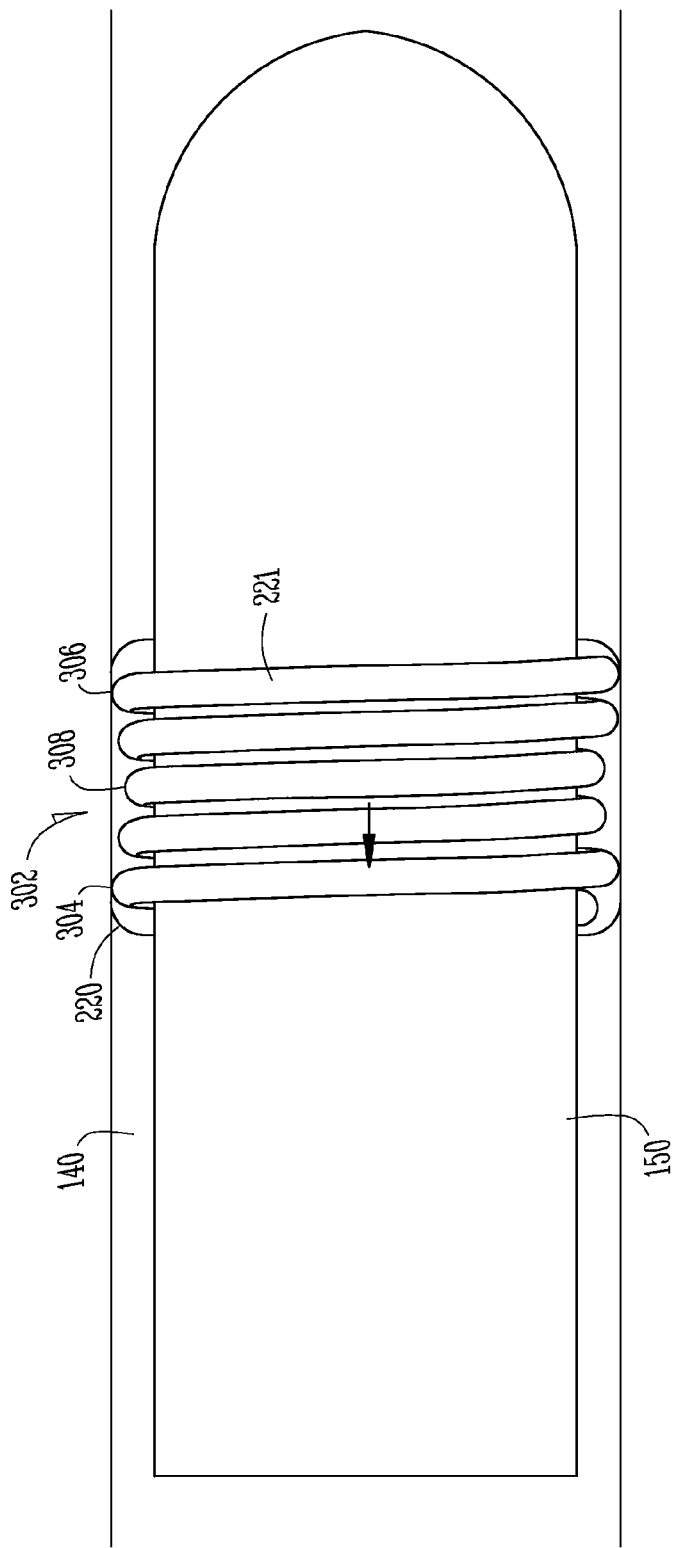

HEADER CONTACT FOR AN IMPLANTABLE DEVICE

CLAIM OF PRIORITY

This application claims the benefit of priority under 35 U.S.C. §119(e) of U.S. Provisional Patent Application Ser. No. 61/664,468, filed on Jun. 26, 2012, which is herein incorporated by reference in its entirety.

BACKGROUND

Leads implanted in or about the heart have been used to reverse certain life threatening arrhythmia, or to stimulate contraction of the heart. Electrical energy is applied to the heart via electrodes on the leads to return the heart to normal rhythm.

A header on an implantable device is used to couple a conductor of the lead with circuitry within the implantable device. For instance, a contact in the header is used to electrically couple a cardiac stimulator system with the lead electrode for making contact with a portion of the heart. U.S. Pat. No. 5,730,628 discusses a header with a leaf spring contact.

Overview

Example 1 can include an implantable medical device including a housing, and a header mounted to the housing, the header including a header body having a bore with an electrical contact located within the bore, wherein the electrical contact includes a helical coil spring having an axial bore, wherein the axial bore of the helical coil spring is aligned with a longitudinal axis of the bore.

In Example 2, the subject matter of Example 1 can optionally include the helical coil spring including an intermediate section having a smaller inner diameter than the diameters of a first end and a second end of the helical coil spring.

In Example 3, the subject matter of Example 2 can optionally include the intermediate section dimensioned such that a terminal inserted into the helical coil spring is gripped by the intermediate section.

In Example 4, the subject matter of any of Examples 1 through 3 can optionally include the helical coil spring mounted within a contact housing.

In Example 5, the subject matter of Example 4 can optionally include the helical coil spring attached by at least a first end or a second end to the contact housing.

In Example 6, the subject matter of any of Examples 1 through 5 can optionally include the helical coil spring having a pitch such that adjacent filars of the helical coil spring do not touch each other during in-vivo use of the electrical contact.

In Example 7, the subject matter of any of Examples 1 through 6 can optionally include the helical coil spring configured to minimize relative motion between an intermediate section of the helical coil spring and a terminal inserted into the helical coil spring.

In Example 8, the subject matter of any of Examples 1 through 7 can optionally include an intermediate turn of the helical coil spring being circular.

In Example 9 the subject matter of any of Examples 1 through 7 can optionally include an intermediate turn of the helical coil spring being elliptical.

In Example 10, the subject matter of any of Examples 1 through 9 can optionally include the helical coil spring mounted within the bore with one of a first end or a second end rigidly fixed and the other of the first end or the second end movable longitudinally within the bore.

In Example 11, the subject matter of any of Examples 1 through 10 can optionally include a lead including a terminal configured to be received within the header bore.

In Example 12, the subject matter of any of Examples 1 through 11 can optionally include the helical coil spring being formed of an MP35N alloy.

In Example 13, an implantable medical device includes a housing, and a header mounted to the housing, the header including a header body having a bore with an electrical contact located within the bore, wherein the electrical contact includes a helical coil spring having an axial bore, wherein the axial bore of the helical coil spring is aligned with a longitudinal axis of the bore, and wherein the helical coil spring includes an intermediate section having a smaller outer diameter than a first end and a second end of the helical coil spring, with the intermediate section being dimensioned such that a terminal inserted into the helical coil spring is gripped by the intermediate section.

In Example 14, the subject matter of Example 13 can optionally include the helical coil spring mounted within a contact housing, with at least one end of the helical coil spring being attached to the contact housing.

In Example 15, the subject matter of Example 13 can optionally include the helical coil spring mounted within a contact housing, and wherein the helical coil spring is not attached to the contact housing.

In Example 16, the subject matter of any of Examples 13 through 15 can optionally include the helical coil spring mounted within the bore with one of the first end or the second end rigidly fixed and the other of the first end or the second end movable longitudinally within the bore.

In Example 17, the subject matter of any of Examples 13 through 16 can optionally include the helical coil spring having a pitch such that adjacent filars of the helical coil spring do not touch each other.

In Example 18 a method includes forming an electrical contact including a helical coil spring having an axial bore, and placing the electrical contact into a header bore of an implantable device, wherein the axial bore of the helical coil spring is aligned with a longitudinal axis of the header bore.

In Example 19, the method of Example 18 can optionally include the helical coil spring including an intermediate section having a smaller outer diameter than a first end and a second end of the helical coil spring.

In Example 20, the method of Example 18 can optionally include the intermediate section being dimensioned such that a lead terminal inserted into the helical coil spring is gripped by the intermediate section and not by the first or second ends of the helical coil spring These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 9 shows a side view of an electrical contact and a terminal inserted within the electrical contact.

FIG. 10 shows a side view of an electrical contact and a terminal inserted within the electrical contact.

DETAILED DESCRIPTION

Figure 1:
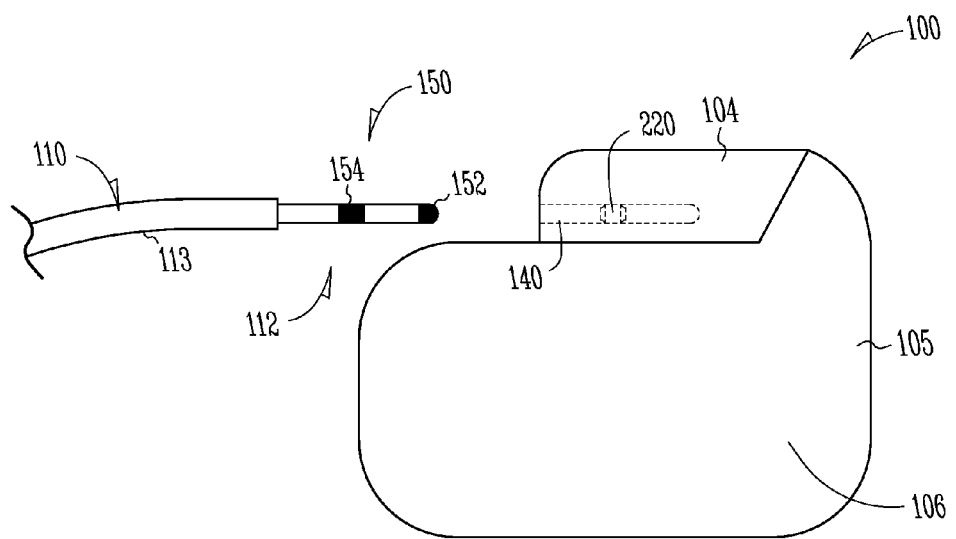
FIG. 1 shows a view of an implantable system according to at least one example.

FIG. 1 shows an implantable system 100, in accordance with one embodiment. The implantable system 100 includes a pulse generator 105 and at least one lead 110. The pulse generator 105 includes a housing 106 and a header 104 mounted to the housing 106. The pulse generator 105 can be implanted into a subcutaneous pocket made in the wall of a patient's chest. Alternatively, the pulse generator 105 can be placed in a subcutaneous pocket made in the abdomen, or in other locations. Pulse generator 105 can include a power supply such as a battery, a capacitor, and other components housed in the housing 106. The pulse generator 105 can include microprocessors to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia.

In other embodiments, implantable system 100 can also be suitable for use with implantable electrical stimulators, such as, but not limited to, neuro-stimulators, skeletal stimulators, central nervous system stimulators, or stimulators for the treatment of pain.

The lead 110 includes a lead body 113 having a proximal end 112, where a terminal 150 of the lead can be coupled to the header 104 of the pulse generator 105. The lead 110 extends to a distal end, which can be coupled with a portion of a heart, when implanted. The distal end of the lead 110 includes at least one electrode which electrically couples the lead 110 with the heart. At least one electrical conductor is disposed within the lead 110 and extends from the proximal end 112 to the electrode. The electrical conductor carries electrical currents and signals between the pulse generator 105 and the electrode.

The header 104 includes one or more bores 140 configured to receive the lead terminal 150 of the lead 110. In this example, the lead terminal 150 includes a proximal tip contact 152, and a terminal ring contact 154. In other examples, the lead terminal 150 can include multiple ring contacts 154. The terminal contacts 152, 154 can be made of stainless steel while insulative portions of terminal 150 can be formed of polyurethane. The terminal ring contact 154 can be coupled via a conductor included in the lead 110.

Figure 2:
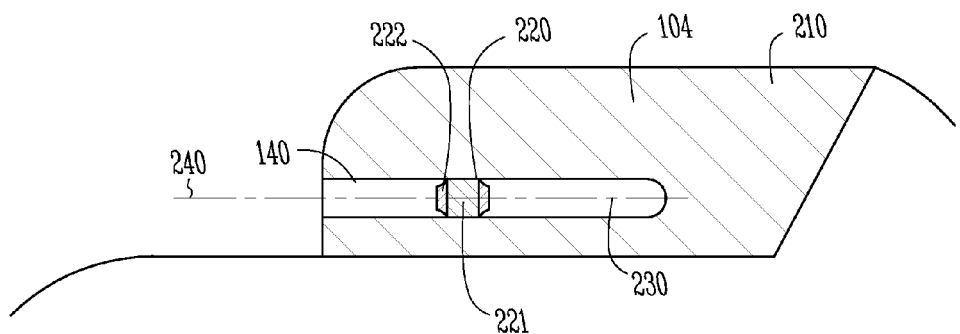
FIG. 2 shows a cross-section side view of a header, in accordance with one example.

FIG. 2 shows an example of a cross-section side view of the header 104. The header 104 can include a header body 210 having the bore 140 formed therein and one or more electrical contacts 220 located within the bore 140 to electrically contact a corresponding contact 154 of the lead 110. The electrical contact 220 can be mounted within a cylindrical, metallic contact housing 222 that can be electrically connected to the electronics in the pulse generator.

The bore 140 can be molded within the body 210 and is sized to receive the terminal 150. In some examples, the bore 140 can include a series of decreasing diameter sections defining a series of steps, with one or more contacts located within each step. Likewise, the terminal 150 can include a stepped design with a series of decreasing diameter portions with one or more contacts on each section. Furthermore, in some embodiments, the system can include an optional set-screw to hold the lead terminal 150 in place within the header 104. Other embodiments can omit the set-screw. In some examples, two or more contacts 220 are located within the bore 140. Other examples can include fewer contacts.

Figure 3:
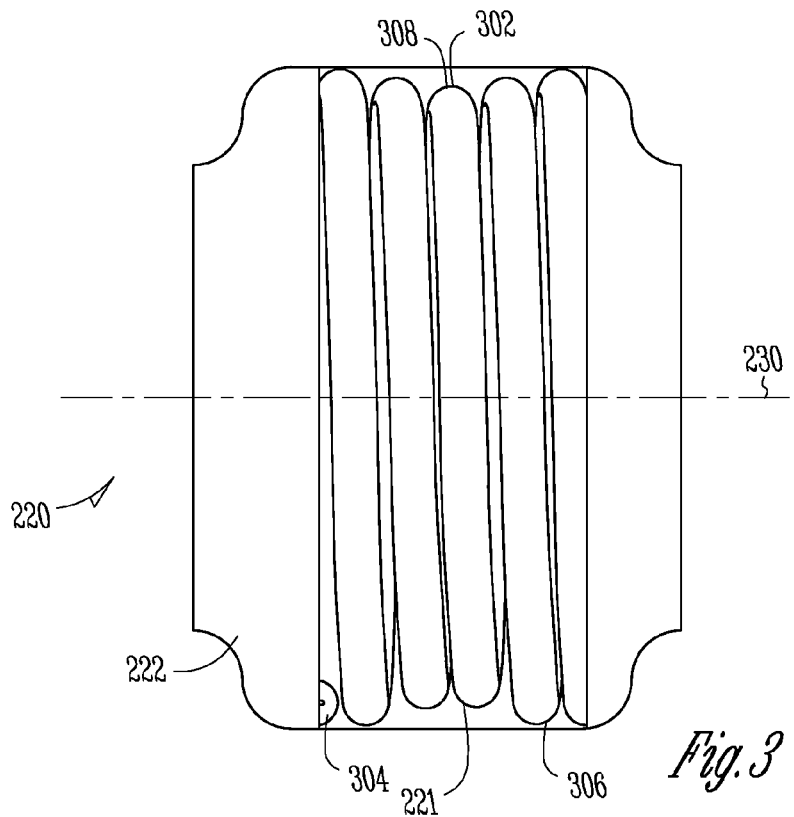
FIG. 3 shows a cross-section of an electrical contact, in accordance with one example.

FIG. 3 shows an example of a cross-section of the electrical contact 220. In an example, the contact 220 is located within the cylindrical contact housing 222 that can be made of MP35N or 316L stainless steel, for example. The cylindrical contact housing 222 can also be formed of other suitable materials. The electrical contact 220 can include a helical coil spring 221 having an axial bore aligned along an axis 230. The axial bore of the helical coil spring 221 can be aligned with a longitudinal axis 240 of the bore 140, as shown in FIG. 2. The helical coil spring 221 has an inner diameter dimensioned to receive the lead terminal 150.

The helical coil spring 221 can include a first end 304 and a second end 306. The helical coil spring can be attached by at least one of the first or second ends to the contact housing 222. The helical coil spring 221 can be mounted within the contact housing 222 with one of a first end 304 or a second end 306 rigidly fixed to the housing and the other of the first end or the second end movable longitudinally within a bore of the contact housing 222. For example, the helical coil spring 221 can be spot welded to the housing 222 on the first end 304 or the second end 306 of the helical coil spring 221, for example. Since the weld only constrains the helical coil spring 221 axially in one spot, the helical coil spring can move axially with the housing 222. In other examples, more than one weld can be used to secure the helical coil spring 221 in the housing 222. In certain examples, no welds are used and the helical coil spring 221 is merely positioned within the contact housing 222 and held by the end walls of the housing 222.

The helical coil spring 221 can include an intermediate section 302 having a smaller outer diameter as compared to a diameter of the first end 304 and the second end 306 of the helical coil spring 221. The diameters of the intermediate section 302 and the first and second ends 304, 306 are chosen such that the intermediate section 302 includes at least one intermediate turn 308 that is dimensioned to contact and grip the terminal 150 in an interference fit while the first end 304 and the second end 306 of the helical coil spring 221 do not grip the lead terminal 150. Such a structure allows the at least one intermediate turn 308 to move axially along axis 230 with the lead terminal 150 when the terminal undergoes the slight in-vivo axially movements that occur when the terminal 150 is mounted within bore 140, and the implantable system 100 is implanted within a body. The intermediate section 302 can be dimensioned such that a terminal inserted into the helical coil spring 221 can be gripped by the intermediate section 302 and not by the first or second ends 304, 306 of the helical coil spring 221.

With past header contacts, such as leaf spring contacts, the contact point between the contact and the terminal remains stationary relative to the header bore when the terminal undergoes any axial movements. This can cause a wearing down of the contact and the terminal at the contact point. The wearing down of the contact point can cause the electrical connection between the terminal and the contact to degrade over time. In contrast, the contact point with the present header contact 220 includes the intermediate turn 308 of the helical coil spring 221. This intermediate turn 308 grips the terminal 150 and moves axially with the lead terminal 150 as the terminal 150 moves axially within the header bore 140. Accordingly, the helical coil spring 221 can be configured to minimize relative motion between the intermediate section 302 of the helical coil spring 221 and the terminal 150 inserted into the helical coil spring 221. Accordingly, any rubbing or wearing between the lead terminal 150 and the contact 220 can be minimized.

In an example, the helical coil spring 221 includes an inner diameter at the intermediate section 302 of about 0.0988 inches (2.51 mm) to about 0.1014 inches (2.576 mm), which corresponds to the size for a 0.106 inch (2.69 mm) lead pin, such as for an IS-1 lead terminal diameter. Other embodiments utilize other diameters, according to lead terminal size, such as for LV-1 leads, and IS-4/DF-4 leads.

In some embodiments, the helical coil spring 221 can be formed of an MP35N alloy. Other example materials include titanium and platinum/iridium, and combinations thereof. The electrical contact 220 can have strength to provide sufficient force at intermediate section 302 against lead terminal ring contact 154 to provide sufficient electrical and mechanical contact between the terminal 150 and the contact 220, while not having an excessive insertion force.

Figure 4:
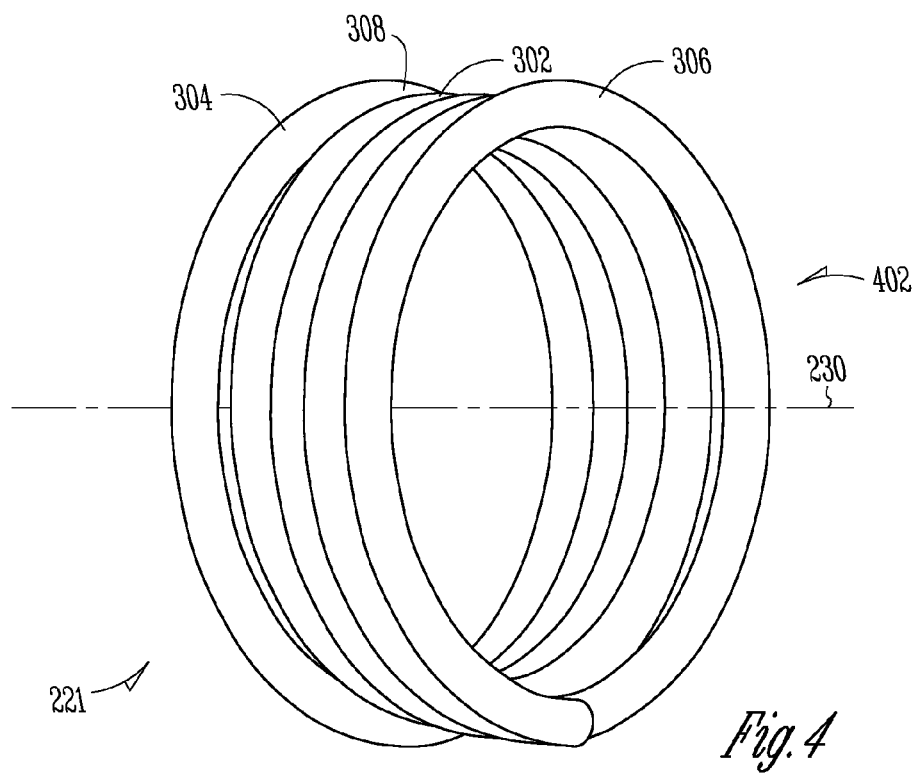
FIG. 4 shows a perspective view of a helical coil spring of the electrical contact of FIG. 3.
Figure 5:
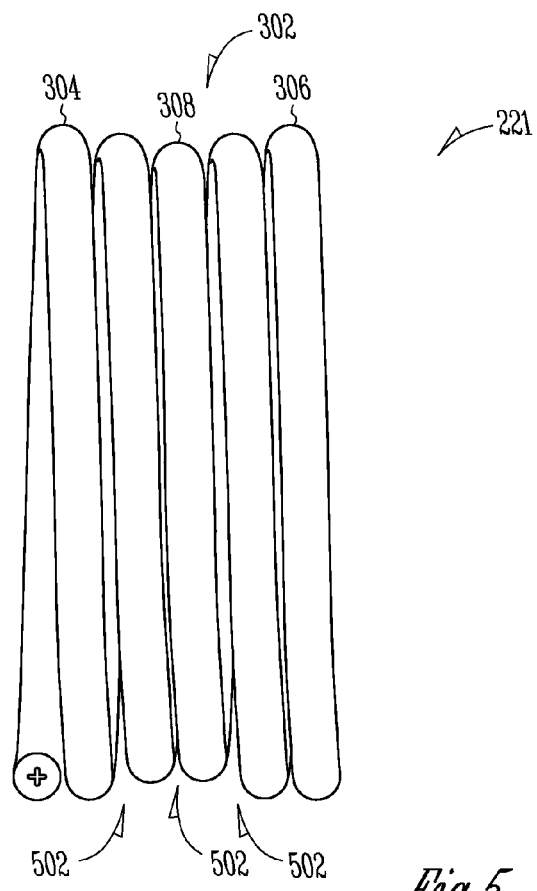
FIG. 5 shows a side view of the helical coil spring of FIG. 3.
Figure 6:
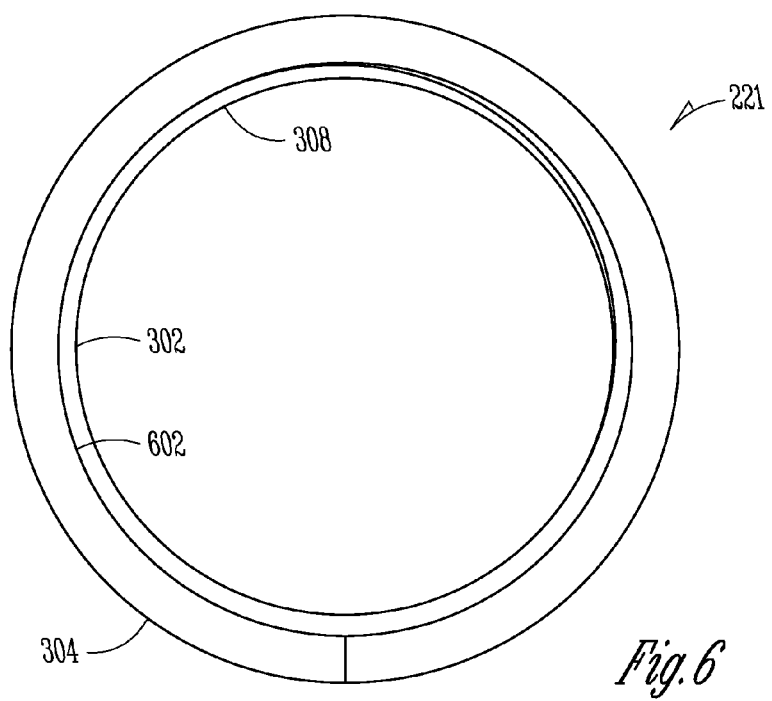
FIG. 6 shows an axial view of the helical coil spring of FIG. 3.

FIG. 4 shows a perspective view of the helical coil spring 221; FIG. 5 shows a side view of the helical coil spring 221; and FIG. 6 shows an axial end view of the helical coil spring 221, according to embodiments of the present disclosure.

In an example, the pitch of the helical coil spring 221 can be dimensioned such that adjacent filars of the helical coil spring 221 do not touch each other due to the axial motion of the lead terminal caused by in-vivo forces. For example, some studies have found that a lead terminal can move about 4 millimeters axially due to in-vivo forces. Thus, based on the relationship that pitch is equal to the sum of the wire diameter and the gap between filars (or likewise, the distance between the centers of adjacent filars), the total gap space of each of gaps 502 (e.g., shown in FIG. 5) can be selected so that it is at least 4 millimeters. Thus, depending on the diameter of the wire chosen for helical coil spring 221, the desired pitch can be determined. The pitch of each of first end 304, intermediate section 302, and the second end 306 can be different than the others, but the total gap size of all the gaps can be greater than 4 millimeters, for example. Providing a large enough pitch so that adjacent filars do not touch during in-vivo axial movement of the terminal allows for the contact 220 to not have any rubbing between the helical coil spring 221 and terminal 150 and also to minimize any wire to wire rubbing of adjacent filars of the helical coil spring 221 itself.

One technique to form the helical wire 221 with the intermediate section 302 having a smaller diameter than the first and second ends 304 and 306 is to use a mandrel having a similar shape as the helical coil spring 221. Wire can be wrapped around the mandrel at the desired pitch and the helical coil spring can be formed. The helical coil spring 221 can then be inserted into the housing 222.

In an example, the intermediate section 302 includes a circular shape 602 so that the lead terminal inserted into the helical coil spring is gripped uniformly by the intermediate turn 308.

Figure 7:
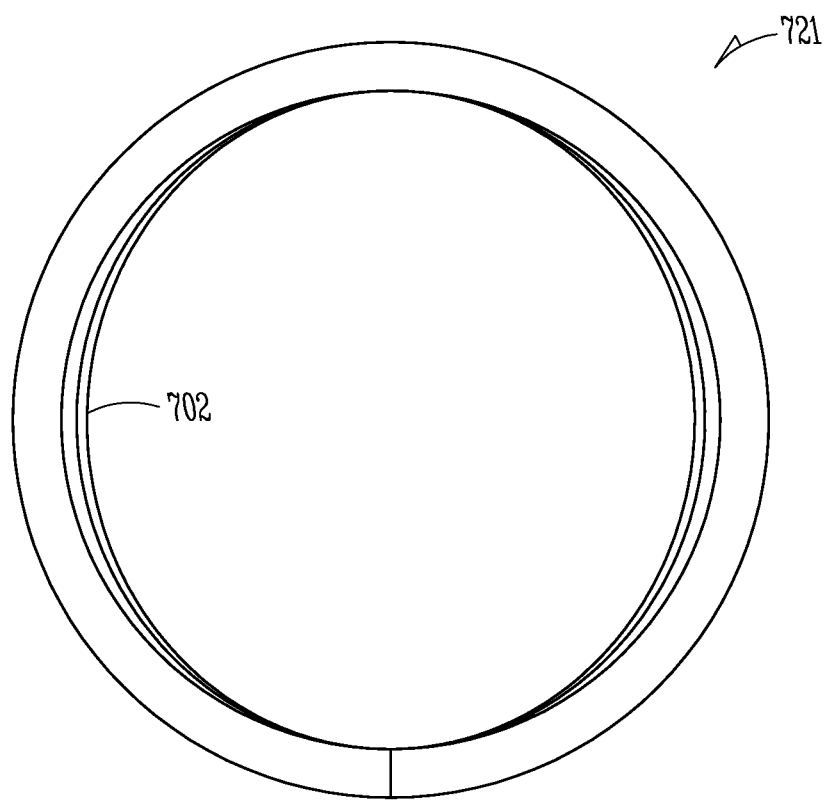
FIG. 7 shows an axial view of a helical coil spring, in accordance with one example.

FIG. 7 shows an axial view of a helical coil spring 721, in accordance with one example. In the helical coil spring 721 the intermediate section 702 includes an intermediate turn 708 having an elliptic shape. Such a structure will grip the terminal at least two points along the terminal, while still allowing the intermediate turn 708 to move axially along with the terminal as the terminal undergoes in-vivo movement.

Figure 8:
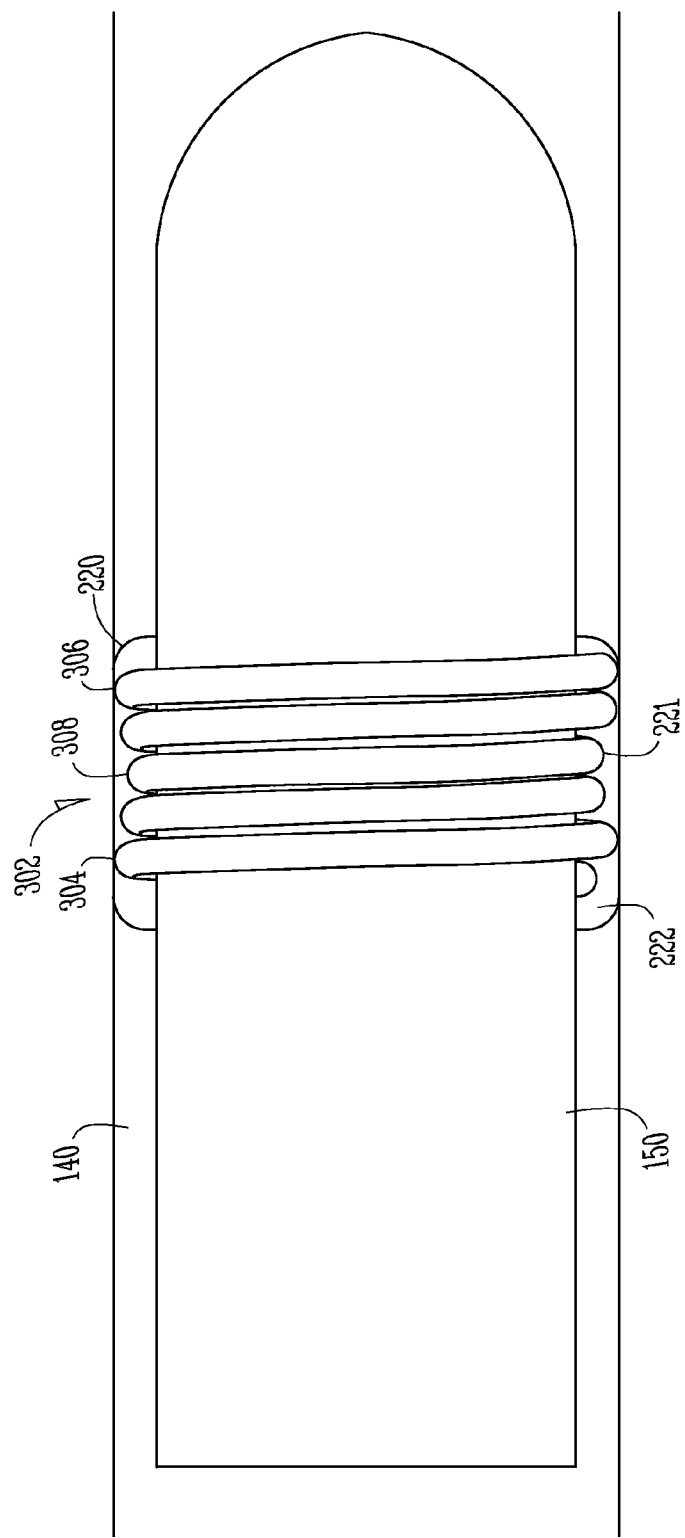
FIG. 8 shows a side view of an electrical contact and a terminal inserted within the electrical contact.

FIG. 8 shows a side view of the electrical contact 220 and the terminal 150 inserted within the helical coil spring 221 within the header bore 140; and FIGS. 9 and 10 shows a side view as the terminal 150 undergoes in-vivo axial movement within the header bore 140.

In use, the lead terminal 150 is inserted into the header bore 140, and the intermediate turn 308 of the intermediate section 302 of the helical coil spring 221 grips the terminal 150. In this example, second end 306 is attached to the housing 222 and the first end 304 is not attached to the housing 222. The first and second ends 304, 306 of the helical coil spring do not grip the terminal 150. Referring to FIG. 9, as the lead terminal 150 moves slightly towards a distal end of bore 140, the intermediate turn 308 moves along with the lead terminal 150 while the first end 304 is drawn along with the intermediate section 302 and the second end 306 compacts. Referring to FIG. 10, as the lead terminal 150 moves slightly towards a proximal end of the bore 140, the intermediate turn 308 moves along with the lead terminal 150 while the first end 304 compacts and the second end 306 stretches. As discussed above, since the gripping intermediate section 302 of the helical coil spring 221 moves with the terminal, there is minimized rubbing between the electrical contact 220 and the terminal 150. Moreover, if a proper pitch is selected for helical coil 221, wire to wire rubbing of the adjacent coil turn of the helical coil spring 221 can be minimized during in-vivo axial movement of the lead terminal 150.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device comprising:
   a housing; and
   a header mounted to the housing, the header including a header body having a bore with an electrical contact located within the bore, wherein the electrical contact includes a helical coil spring having a helical coil formed of a plurality of coils with an axial bore through a center area of each of the plurality of coils of the helical coil, wherein the axial bore of the helical coil spring is aligned with a longitudinal axis of the bore and positioned and configured to receive a terminal through a center of the axial bore at the center area of the helical coil, and wherein the helical coil includes an intermediate section having a smaller inner diameter as compared to a diameter of a first end and a diameter of a second end of the helical coil spring and the helical coil spring has a pitch such that adjacent filars of the helical coil spring do not touch each other.

2. The implantable medical device of claim 1, wherein the helical coil spring is formed of an MP35N alloy.

3. The implantable medical device of claim 1, wherein the intermediate section is dimensioned such that a terminal inserted into the helical coil spring is gripped by the intermediate section.

4. The implantable medical device of claim 1 wherein the helical coil spring is mounted within a contact housing.

5. The implantable medical device of claim 4, wherein the helical coil spring is attached by at least one of a first end or a second end to the contact housing.

6. The implantable medical device of claim 1, further including a lead including a terminal configured to be received within the bore.

7. The implantable medical device of claim 1, wherein the helical coil spring is configured to minimize relative motion between an intermediate section of the helical coil spring and a terminal inserted into the helical coil spring.

8. The implantable medical device of claim 1, wherein an intermediate turn of the helical coil spring is circular.

9. The implantable medical device of claim 1, wherein an intermediate turn of the helical coil spring is elliptical.

10. The implantable medical device of claim 1, wherein the helical coil spring is mounted within the bore with one of a first end or a second end rigidly fixed and the other of the first end or the second end movable longitudinally within the bore.

11. An implantable medical device comprising:
    a housing; and
    a header mounted to the housing, the header including a header body having a bore with an electrical contact located within the bore, wherein the electrical contact includes a helical coil spring having a helical coil formed of a plurality of coils with an axial bore through a center area of each of the plurality of coils of the helical coil and positioned and configured to receive a terminal through a center of the axial bore at the center area of the helical coil, wherein the axial bore of the helical coil spring is aligned with a longitudinal axis of the bore, and wherein the helical coil spring includes an intermediate section having a smaller outer diameter than a first end and a second end of the helical coil spring, with the intermediate section being dimensioned such that a terminal inserted into the helical coil spring is gripped by the intermediate section and the helical coil spring has a pitch such that adjacent filars of the helical coil spring do not touch each other.

12. The implantable medical device of claim 11, wherein the helical coil spring is mounted within a contact housing, with at least one of a first end or a second end of the helical coil spring being attached to the contact housing.

13. The implantable medical device of claim 11, wherein the helical coil spring is mounted within a contact housing, and wherein the helical coil spring is not attached to the contact housing.

14. The implantable medical device of claim 11, wherein the helical coil spring is mounted within the bore with one of the first end or the second end rigidly fixed and the other of the first end or the second end movable longitudinally within the bore.

15. A method comprising:
    forming an electrical contact including a helical coil spring having a helical coil formed of a plurality of coils with an axial bore through a center area of each of the plurality of coils of the helical coil; and
    placing the electrical contact into a header bore of an implantable device, wherein the axial bore of the helical coil spring is aligned with a longitudinal axis of the header bore and positioned and configured to receive a terminal through a center of the axial bore at the center area of the helical coil, wherein the helical coil includes an intermediate section having a smaller inner diameter as compared to a diameter of a first end and a diameter of a second end of the helical coil spring and the helical coil spring has a pitch such that adjacent filars of the helical coil spring do not touch each other.

16. The method of claim 15, wherein the intermediate section is dimensioned such that a lead terminal inserted into the helical coil spring is gripped by the intermediate section and not by the first or second ends of the helical coil spring.

* * * * *